United States Patent [19]

Singh et al.

[11] Patent Number: 5,527,920

[45] Date of Patent: Jun. 18, 1996

[54] ECONOMICAL MANUFACTURING PROCESS FOR 1,2,3-TRIAZOLES

[76] Inventors: Inder P. Singh, 4624 - 43A Avenue, Edmonton, AB T6L 6L9, Canada; Paul Spevak, 5504 - 174 Street, Edmonton, AB T6M 1H9, Canada; Bhupinder Palak, 3309 - 44A Street, Edmonton, AB T6L 4X1, Canada; Samuel Amedjo, 9531 - 152 Street, Edmonton, AB T5P 1W6, Canada; Ronald G. Micetich, 12 Braeside Terrace, Sherwood Park, AB T8A 3V6, Canada

[21] Appl. No.: 344,586

[22] Filed: Nov. 18, 1994

[51] Int. Cl.$^6$ ................................. C07D 249/06
[52] U.S. Cl. ................................................ 548/255
[58] Field of Search ...................................... 548/255

[56] References Cited

U.S. PATENT DOCUMENTS

| | | | |
|---|---|---|---|
| 4,515,799 | 5/1985 | Campbell et al. | 514/341 |
| 4,590,203 | 5/1986 | Binder et al. | 514/397 |
| 4,857,539 | 8/1989 | Diana et al. | 514/378 |
| 5,315,013 | 5/1994 | Carini et al. | 548/376.1 |

FOREIGN PATENT DOCUMENTS

| | | | |
|---|---|---|---|
| 323841 | 7/1989 | European Pat. Off. | C07D 249/02 |
| 533268 | 3/1992 | European Pat. Off. | C07D 271/06 |
| 9209600 | 6/1992 | WIPO | C07D 405/06 |

*Primary Examiner*—Jacqueline Haley
*Attorney, Agent, or Firm*—Nikaido, Marmelstein, Murray & Oram

[57] ABSTRACT

A high quality 1,2,3-triazole is obtained in a one pot two step reaction between appropriately substituted hydrazide derivatives, dihaloethanediol and $NH_3$ in methanol. Synthesis of various $N_1$-alkyl, $N_1$-aryl, and $N_1$-heterocyclic-1,2,3-triazoles is also accomplished following the same general procedure.

19 Claims, No Drawings

ECONOMICAL MANUFACTURING PROCESS FOR 1,2,3-TRIAZOLES

BACKGROUND OF THE INVENTION

1. Field of the Invention

The present invention is concerned with the production of 1,2,3-triazoles by a simple, economical and safe method.

The unsubstituted 1,2,3-triazole is utilized in the preparation of important pharmaceutical compounds such as the beta-lactamase inhibitor, Tazobactam (Ger. Offen. DE 2943427, 800508 EP 331395 AI 890906). The substituted triazoles can be used as intermediates in the preparation of various other pharmaceuticals or pesticides (JP 05222006 A2 930831 Heisei, JP 05148280 A2 930615 Heisei, JP 05112536 A2 930507 Heisei and EP 433842 A2 910626).

2. Description of Related Art

One of the current methods used for the preparation of triazoles is by the reaction of acetylene and azide derivatives followed by reductive cleavage of the protecting group (Japan Kokai Tokyo Koho JP 1-143861). The chemicals used have an explosive nature and the process employs hazardous conditions.

Another method of preparation utilizes dichloroacetaldehyde and sulfonyl hydrazide (Japan Kokai Tokyo Koho JP 5-140121). The preparation requires two steps. The reactions used are summarized below:

Step I

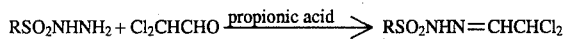

Step II

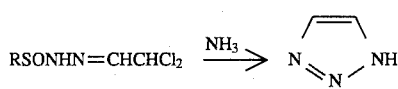

The above process has the following disadvantages:

1. It employs dichloroacetaldehyde, that is toxic and has a tendency to polymerize in the presence of acids and also on storage.
2. The process requires two steps and these two steps require two different solvents.
3. The removal of propionic acid (the solvent) from the hydrazone product of the first step is difficult on a production scale. The removal requires large amounts of hexane to wash out the propionic acid.
4. Any remaining propionic acid leads to the formation of side products that contaminate the final product.
5. The described method requires the isolation of triazoles using column chromatography and this increases cost, particularly for large scale preparations.

SUMMARY OF THE INVENTION

A high quality 1,2,3-triazole is obtained in a one pot two step reaction between appropriately substituted hydrazide derivatives, dichloroethanediol and $NH_3$ or amines in methanol. Synthesis of various $N_1$-alkyl, $N_1$-aryl, and $N_1$-heterocyclic-1,2,3triazole is also accomplished following the same general procedure.

The principal reaction that takes place is summarized below:

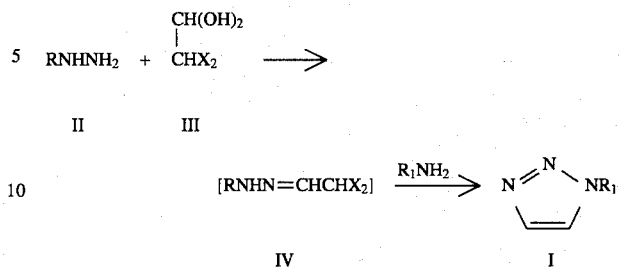

The present invention provides an improved, safer and economical one pot method for the production of triazoles and has the following advantages:

1. It utilizes dihaloethanediol instead of dichloroacetaldehyde. Dihaloethanediol is less toxic and does not tend to polymerize on standing over a long period of time.
2. The method provides a one pot synthesis process.
3. The method utilizes one solvent for both steps and needs no isolation and further purification of the intermediate hydrazone, generated in situ. This intermediate can also be isolated easily in pure form and can be used for the synthesis of other N-substituted triazoles.
4. In addition to sulfonyl hydrazides, readily available and cheaper substituted carboxylic acid hydrazides can also be used.

DESCRIPTION OF THE PREFERRED EMBODIMENTS

The principal reaction that takes place is summarized below:

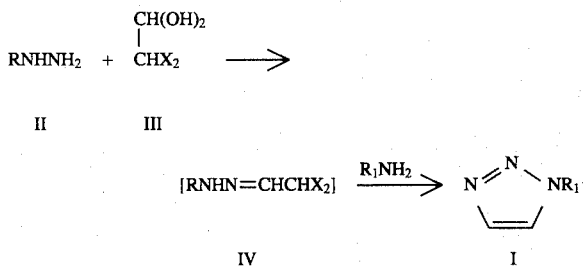

A typical method of producing 1,2,3-triazole (I) is by the addition of a dihaloethanediol into a solution of an appropriately substituted hydrazide and then bubbling ammonia through it to give the triazole. When an appropriately substituted amine is added in place of ammonia, the corresponding $N_1$-substituted triazole is formed. The triazole is isolated from the reaction mixture by distillation, and substituted triazoles can be isolated by distillation or by column chromatography. The whole process is done with or without an acid or base catalyst.

The hydrazides used in this process are of the general formula II, wherein R represents R'CO or $R'SO_2$; wherein R' can be a lower alkyl such as methyl, ethyl, propyl, isopropyl, or butyl which may be substituted with halogens such as chloro, bromo or fluoro; or a phenyl group that can be substituted with chloro, fluoro, bromo, nitro, lower alkyl or lower alkoxy.

The dihaloethanediols used in this process are of general formula III, wherein X represents any of chloro, bromo or fluoro substituent.

The amines used in this process are of general formula $R_1NH_2$, where $R_1$ represents H, alkyl, aryl or heterocyclic groups. The alkyl group can be methyl, ethyl, propyl, cyclopropyl, isopropyl, butyl, or t-butyl which may be substituted with a phenyl group that can be further substituted with chloro, fluoro, bromo, nitro, lower alkyl or lower alkoxy. $R_1$ can also be phenyl or a phenyl that is further substituted with at least one of chloro, fluoro, bromo, nitro, lower alkyl or lower alkoxy group. $R_1$ may also be a heterocyclic group. Preferred heterocyclic groups are thiophene, thiazole, triazole, thiadiazole, oxazole, oxadiazole, imidazole, isoxazole, isothiazole, pyridine and piperidine.

The ammonia used in this reaction can be in the gaseous form and bubbled directly into the reaction mixture or liquid ammonia or a solution of ammonia in water or in a suitable organic solvent. The substituted amines can be added as solids, liquids, gas or in solution in water or suitable organic solvents.

The solvents used in the procedure of the present invention can be water or any one of the following or mixtures thereof: lower alkanols such as methanol, ethanol, propanol, isopropanol, or butanol; alkyl ethers such as diethyl, ethyl methyl, or isopropyl ether; halogenated hydrocarbons, especially halogenated lower alkanes such as dichloromethane, chloroform, or carbon tetrachloride; and other solvents such as DMSO, DMF, $CH_3CN$, dioxane or diphenyl ether.

The molar ratio of dihaloethanediol to hydrazide may vary, for instance, from 1:1 to 1:10, however, 1 mole of dihaloethanediol for every one mole of hydrazide is preferred.

The temperature during the first part of reaction when a hydrazide is mixed with diol ranges from 0° C. to 25° C. The reaction temperature during the second part of the reaction when ammonia is added to reaction mixture may vary from −30° to 70° C., but the preferred temperature is between 20 to 40° C. The time for the reaction varies with the reactants and the solvents and catalyst, if a catalyst is used. However, overall reaction time from 1 to 20 hrs. is preferred.

The method of reacting the hydrazide derivatives with dihaloethanediol can be varied. For example, both may be dissolved simultaneously into a solvent and, after the initial reaction is over, ammonia is bubbled through. Alternatively, a solution of hydrazide is added to a solution of dihaloethanediol, or vice versa, and then $NH_3$ is added as a gas or in a solution form. The reaction mixture is cooled to −30° C. if liquid ammonia is to be used.

The reaction can be conducted in the presence of acid catalysts, such as an organic carboxylic acid or a mineral acid; in the presence of basic catalyst, such as ammonia or an alkali metal hydroxide; or without using any catalyst.

The triazole is preferably isolated from the reaction mixture in the following way. The ammonia and the solvent, if low boiling, are removed by distillation, and the residue extracted with a mixture of methanol and ether or with chloroform or methylene chloride. The extract is then concentrated. The triazole is obtained in 35 to 55% yields by fractional distillation of the oily residue.

The N-alkyl or N-aryl triazoles are isolated as described above or by column chromatography. Suitable materials for the column chromatography include normal-phase adsorbents such as silica gel, alumina, and reversed phase adsorbents such as C-18, etc. The mobile phase may be any of the following: hexane, $CCl_4$, $CH_2$, $Cl_2$, $CHCl_3$, methanol or higher alkyl alcohols, ethyl acetate or a mixture thereof. Other possible mobile phases are water, buffer, or their combination, with suitable organic acids or bases.

The organic carboxylic acids used in this process can be aliphatic carboxylic acids such as formic, acetic, propionic, isopropionic, butyric or isobutyric acid; aromatic carboxylic acids; aliphatic or aromatic sulfonic acids or a mixture thereof. Inorganic mineral acids, such as hydrochloric acid or sulfuric acid, may also be used.

EXAMPLE 1

Dichloroethanediol (3.52 gm) was added dropwise to a solution of p-toluene sulfonyl hydrazide (5 gm) and glacial acetic acid (0.25 ml) in methanol (90 ml). The reaction mixture was then stirred for an additional 15 minutes. A stream of ammonia was bubbled through the reaction mixture, maintaining the temperature under 40° C. for 30 minutes. The reaction mixture was left stirring at room temperature overnight. Ammonia and methanol were recovered under vacuum and the remaining residue dissolved in a mixture of 25% methanol in ether (250 ml. The separated solid was removed by filtration, the filtrate concentrated, and the residue distilled under vacuum for the isolation of triazole (yield 44%). NMR ($CDCl_3$) δ: 7.76 ppm (2H).

EXAMPLE 2 p-Toluene sulfonyl hydrazide (5 gm) was added portionwise into a solution of dichloroethanediol (3.52 gm) and glacial acetic acid (0.25 ml) in methanol (90 ml). The reaction mixture was then stirred for an additional 15 minutes. A stream of ammonia was bubbled through the reaction mixture, maintaining the temperature under 40° C. for 30 minutes. The reaction mixture was left with stirring at room temperature overnight. Ammonia and methanol were recovered under vacuum and the remaining residue dissolved in a mixture of 25% methanol in ether (250 ml). The separated solid was removed by filtration, the filtrate concentrated, and the residue distilled under vacuum for the isolation of triazole (yield 55.4%). NMR (CDCl3) δ: 7.76 ppm (2H).

EXAMPLE 3

Dichloroethanediol was added dropwise (2.54 gm) while stirring to a solution of p-chlorobenzene sulfonyl hydrazide (4 gm) and formic acid (0.30 ml) in 40 ml of methanol. The reaction mixture was stirred for an additional 30 minutes. Ammonia was bubbled slowly through the resultant suspension, to maintain the temperature between 20 and 35° C. The bubbling of ammonia was stopped after 25 minutes. The resultant clear reaction mixture was then left with stirring at room temperature for 17 hours. The solvent was removed and the residue extracted with ether. The ether extract was concentrated and the 1,2,3-triazole was recovered from the oily residue by fractional distillation under high vacuum (yield 22.8%). NMR ($CDCl_3$) δ: 7.76 ppm (2H).

EXAMPLE 4

Dichloroethanediol (4.3 gm) was added dropwise into a solution of m-nitro-benzoic acid hydrazide (6 gm) and acetic acid (0.25 ml) in methanol (90 ml) at 40° C. The reaction mixture was then stirred for an additional 15 minutes. A stream of ammonia was bubbled through the reaction mixture, maintaining the temperature under 40° C. for 35 minutes. The reaction mixture was left with stirring at room temperature overnight. The separated solid was removed by filtration and washed with ether, the filtrate was concentrated to an oily residue. 1,2,3-triazole was recovered by fractional distillation of the residue under vacuum (yield 18.16%). NMR (CDCl$_3$) δ: 7.77 ppm (2H).

EXAMPLE 5

To a solution of p-toluene sulfonyl hydrazide (5 gm, 0.0268 m) and acetic acid (1.0 ml) in 75 ml of methanol, dichloroethanediol (3.52 gm) was added dropwise over 5 minutes while stirring. The reaction mixture was stirred for an additional 60 minutes. To the resultant suspension, benzyl amine (8.61 gm, 0.0804 m) was added at once. The resultant reaction mixture was then left with stirring at room temperature for 18 hours. The solvent was removed and the residue extracted with ether. The ether extract was concentrated and N-benzyl-1,2,3-triazole was recovered from the oily residue by distillation under high vacuum (yield 41.7%). NMR (CDCl3) δ: 5.52 (s, 2H), 7.34 (m, 5H), 7.55 (s, 1H), 7.72 (s, 1H) ppm.

EXAMPLE 6

To a solution of p-toluene sulfonyl hydrazide (5 gm) in methanol (100 ml), concentrated sulfuric acid (2.63 gm) was added and the reaction mixture cooled to 15° C. To the reaction solution dichloroethanediol was added dropwise (5.28 gm) while stirring over 5 minutes. After 18 hours of stirring at 15° C., the separated solid was removed by filtration. Filtrate was concentrated and the residue extracted with diethyl ether. Ether layer was washed with water and brine, dried over sodium sulfate, concentrated to give pure 2,2-dichloroacetaldehyde p-toluene sulfonyl hydrazone (yield 72.3%), mp. 123° C.

EXAMPLE 7

To a cooled solution of 2,2-dichloroacetaldehyde p-toluene sulfonyl hydrazone (1 gm, 0.0039 m) in methanol (10 ml), ethyl amine (0,726 gm, 0.0161 m) was added dropwise while maintaining the temperature of the reaction under 10° C. The temperature of the reaction mixture was raised slowly to room temperature over 30 minutes, and stirring continued for an additional 20 hours. The solvent was removed and the residue extracted with ether. The ether extract was concentrated and the N$_1$-ethyl, 1,2,3-triazole recovered from the oily residue by chromatography over a silica gel column (yield 210 mg, 60.86%). NMR (CDCl$_3$) δ: 1.56 (t, 3H), 4.47 (q, 2H), 7.60 (s, 1H), 7.7 (s, 1H) ppm.

EXAMPLE 8

To a cooled solution of 2,2-dichloroacetaldehyde p-toluene sulfonyl hydrazone (1 gm, 0.0039 m) in methanol (10 ml), cyclopropyl amine (0.92 gm, 0.0161 m) was added dropwise while maintaining the temperature of the reaction under 10° C. The temperature of the reaction mixture was raised slowly to room temperature over 30 minutes, and stirring continued for an additional 20 hours. The solvent was removed and the residue extracted with ether. The ether extract was concentrated and the N$_1$-cyclopropyl-1,2,3-triazole was recovered from the oily residue by chromatography over a silica gel column (yield 186 mg, 48.06%). NMR (CDCl$_3$) δ: 1.26 (m, 4H), 3.78 (m, 1H), 7.6 (s, 1H), 7.66 (s, 1H) ppm.

EXAMPLE 9

To a cooled solution of 2,2-dichloroacetaldehyde p-toluene sulfonyl hydrazone (1 gm, 0.0537 m) in methanol (10 ml), 2-amino thiazole (1.6 gm, 0.0161 m) was added portionwise while maintaining the temperature of the reaction under 10° C. The temperature of the reaction mixture was raised slowly to the room temperature over 30 minutes, and stirring continued for an additional 20 hours. The solvent was removed and the residue extracted with ether. The ether extract was concentrated and the N$_1$-thiazol-2-yl-1,2,3-triazole was recovered from the oily residue by chromatography over a silica gel column (yield 320 mg, 38.39%). NMR (CDCl$_3$) δ: 7.29 (d, 1H), 7.68 (d, 1H), 7.84 (s, 1H), 8.44 (s, H) ppm.

We claim:

1. A method of producing a 1,2,3-triazole, N$_1$-phenyl-1, 2,3-triazole, N$_1$-napthyl-1,2,3-triazole, N$_1$-alkyl 1,2,3-triazole or N$_1$-heterocyclic-1,2,3-triazole comprising:

reacting a hydrazide of formula II    (II)
RNHNH$_2$ with a dihaloethanediol of formula III    (III)
CH(OH)$_2$
|
CHX$_2$ and ammonia or an amine of formula R$_1$NH$_2$ wherein R is R'CO or R'SO$_2$; and R' is a C$_1$–C$_6$ alkyl which is unsubstituted or substituted with at least one halogen, or R' is a phenyl group which is unsubstituted or substituted with Cl, F, Br, nitro, C$_1$–C$_6$ alkyl or C$_1$–C$_6$ alkoxy; X is Cl, F, or Br; and R$_1$ is H, C$_1$–C$_6$ alkyl which is unsubstituted or substituted with a phenyl group and the phenyl group is unsubstituted or substituted with chloro, fluoro, bromo, nitro, C$_1$–C$_6$ alkyl or C$_1$–C$_6$ alkoxy, or R$_1$ is phenyl which is unsubstituted with at least one of chloro, fluoro, bromo, nitro, C$_1$–C$_6$ alkyl or C$_1$–C$_6$ alkoxy, or R$_l$ is napthyl, or a heterocyclic group.

2. The method of claim 1 comprising:

a) adding p-toluene sulfonyl hydrazide to a solution of dichloroethanediol in the presence of acetic acid; and b) subsequently adding NH$_3$ gas.

3. The method of claim 1 comprising adding, in one step, NH$_3$ gas to a mixture of p-toluene sulfonyl hydrazide and dichloroethanediol in the presence of acetic acid.

4. The method of claim 1 comprising:

a) adding dichloroethanediol solution to a solution of p-chlorobenzene sulfonyl hydrazide in the presence of formic acid, and b) subsequently adding NH$_3$ gas.

5. The method of claim 1 comprising a) adding dichloroethanediol solution to a solution of p-chlorobenzene sulfonyl hydrazide in the presence of acetic acid, and b) subsequently adding NH$_3$ gas.

6. The method of claim 1 comprising a) adding dichloroethanediol to a solution of m-nitrobenzoic acid hydrazide in the presence of acetic acid, and b) subsequently adding ammonia gas.

7. The method of claim 1 comprising a) adding dichloroethanediol to a solution of p-toluene sulfonyl hydrazide in the presence of acetic acid, and b) subsequently adding NH$_3$ gas.

8. The method of claim 1 comprising a) adding solid p-toluene sulfonyl hydrazide to a stirred solution of dichloroethanediol and acetic acid in methanol, and b) subsequently adding ammonia gas.

9. The method of claim 1 for producing N$_1$-benzyl-1,2, 3-triazole comprising reacting dichloroethanediol, p-toluene sulfonyl hydrazide and benzyl amine to give $N_1$-benzyl-1,2,3-triazole.

10. The method of claim 1 wherein the method is carried out in one reaction vessel.

11. The method of claim 1 wherein R' is selected from the group consisting of methyl, ethyl, propyl, isopropyl, or butyl, which is unsubstituted or substituted with at least one of chloro, bromo, or fluoro.

12. A method of forming a hydrazone of formula $RNHN=CHCHX_2$ comprising

> reacting a hydrazide of formula II (II)
> $RNHNH_2$
>
> with a dihaloethanediol of formula III (III)
> $CH(OH)_2$
> |
> $CHX_2$ wherein R is R'CO or R'SO$_2$; and R' is a $C_1$–$C_6$ alkyl which is unsubstituted or substituted with at least one halogen, or R' is a phenyl group which is unsubstituted or substituted with Cl, F, Br, nitro, $C_1$–$C_6$ alkyl or $C_1$–$C_6$ alkoxy; and X is Cl, F, or Br.

13. The method of claim 12 for making dichloroacetaldehyde-p-toluene-sulfonyl hydrazone in high yield comprising adding dichloroethanediol to a solution of p-toluene sulfonyl hydrazide in the presence of sulfuric acid.

14. A method for producing $N_1$-aryl 1,2,3-triazole, $N_1$-alkyl 1,2,3-triazole or $N_1$-heterocyclic-1,2,3-triazole comprising reacting dichloroacetaldehyde-p-toulene-sulfonyl-hydrazone and an amine of the formula $R_1NH_2$ wherein $R_1$ is selected from the group consisting of $C_1$–$C_6$ alkyl wherein the alkyl is selected from the group consisting of methyl, ethyl, propyl, cyclopropyl, isopropyl, butyl, and t-butyl and wherein the alkyl is unsubstituted or substituted with a phenyl group that can be further substituted with chloro, fluoro, bromo, nitro, lower alkyl or lower alkoxy; phenyl which is unsubstituted or substituted with at least one of chloro, fluoro, bromo, nitro, lower alkyl or lower alkoxy; naphthyl, and a heterocyclic group selected from the group consisting of thiophene, thiazole, triazole, triadiazole, oxazole, oxidiazole, inidazole, isoxazole, isothiazole, pyridine, and piperidine; to give the product.

15. The method of claim 14 wherein $R_1$ is ethyl, benzyl, cyclopropyl, or thiazolyl.

16. The method of claim 1 wherein the reaction is carried out at between −30° and 70° C.

17. The method of claim 12 wherein the reaction is carried out at between 0° and 25° C.

18. The method of claim 14 wherein the reaction is carried out at between −30° and 70° C.

19. The method of claim 14 wherein the reaction is carried out at between 20° and 40° C.

* * * * *